United States Patent [19]

Renga et al.

[11] 4,349,482
[45] * Sep. 14, 1982

[54] PROCESS FOR MAKING VICINAL EPOXIDES AND DIHALIDES

[75] Inventors: James M. Renga; Albert H. Emmons, both of Midland, Mich.

[73] Assignee: The Dow Chemical Co., Midland, Mich.

[*] Notice: The portion of the term of this patent subsequent to Apr. 14, 1998, has been disclaimed.

[21] Appl. No.: 238,188

[22] Filed: Feb. 25, 1981

Related U.S. Application Data

[63] Continuation-in-part of Ser. No. 95,002, Nov. 16, 1979, Pat. No. 4,261,906.

[51] Int. Cl.³ .................................. C07D 301/02
[52] U.S. Cl. .................................. 549/518
[58] Field of Search .................. 260/348.16

[56] References Cited

U.S. PATENT DOCUMENTS 4,069,234  1/1978  Wu .................. 260/348.16

FOREIGN PATENT DOCUMENTS 53-46921  4/1978  Japan .

*Primary Examiner*—Norma S. Milestone
*Attorney, Agent, or Firm*—David H. Thurston; Douglas N. Deline

[57] ABSTRACT

Vicinal epoxides and alkylene dihalides are produced by decomposing a β-haloalkyl carbonate of the general formula

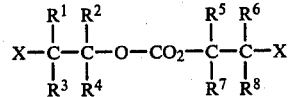

in the presence of a quaternary ammonium or phosphonium salt.

10 Claims, No Drawings

PROCESS FOR MAKING VICINAL EPOXIDES AND DIHALIDES

CROSS-REFERENCE TO RELATED APPLICATION

This is a continuation-in-part of our application Ser. No. 095,002 filed Nov. 16, 1979, now Pat. No. 4,261,906.

BACKGROUND OF THE INVENTION

This invention relates to a new process for making vicinal epoxides and alkylene dihalides.

Vicinal epoxides are valuable chemical intermediates and monomers useful in making epoxy adhesives and various heat- and solvent-resistant polymers. A well-known process for making vicinal epoxides from olefins involves the oxidation of the olefinic double bond with aqueous chlorine to form the chlorohydrin and reaction of the chlorohydrin with a base to make the epoxide. However, a major disadvantage of this process is the production of an equivalent of HCl from the aqueous oxychlorination step and another equivalent of inorganic chloride from the reaction of the base with the chlorohydrin intermediate. In the case of epichlorohydrin, the conventional preparation uses the same chemistry with the added initial step of chlorinating propylene to allyl chloride which produces an additional equivalent of HCl.

Ethylene oxide is prepared by oxidizing ethylene with molecular oxygen over a silver catalyst. However, this method is not applicable to other olefins because of low selectivity and the formation of by-products. Another method using oxygen involves oxidizing a hydrocarbon such as isobutane or isopropylbenzene with air to the corresponding tertiary hydroperoxide and then reacting the hydroperoxide with an olefin in the presence of a transition metal catalyst. A disadvantage of this process is the formation of co-product alcohol which must be sold or recycled.

Hydrogen peroxide and peroxy acids are other reagents which have been used to epoxidize olefins. Chemical and economic disadvantages of such methods have precluded their use on a large scale.

It is known that cyclic carbonates can be decomposed to form epoxides in the presence of various catalysts. Such a process particularly directed to the preparation of propylene oxide by decomposition of propylene carbonate in the presence of a sulfonium or phosphonium halide or any of certain metal salts is described in U.S. Pat. No. 4,069,234.

In our related application cited above, it has been shown that vicinal epoxides of various kinds, not only the simple alkylene and cycloalkylene oxides, but also their aromatic and halogen-substituted derivatives, can be made in good yield by heating an unsymmetrical β-haloalkyl carbonate of the formula

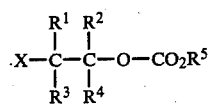

in the presence of a small but effective amount of a quaternary ammonium or phosphonium salt at a temperature of about 25° C.–250° C. The products of this decomposition are $CO_2$, the halide $R^5X$, and the epoxide of the formula

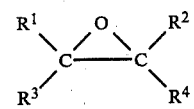

wherein X is Cl or Br, each of $R^1$, $R^2$, $R^3$, and $R^4$ is hydrogen, a hydrocarbon group, $-CH_2X$, or $R^1$ and $R^2$ together form an alkylene group of 3-6 carbon atoms, and $R^5$ is an alkyl group, preferably a lower alkyl group.

SUMMARY OF THE INVENTION

It has now been found that the above-described carbonate decomposition reaction is modified when $R^5$ in the carbonate formula is also a β-haloalkyl group as defined therein, the products of the decomposition reaction then being a vicinal epoxide, $CO_2$, and an alkylene dihalide. When the two haloalkyl groups in the carbonate molecule are of unequal size, for example, as in a haloethyl halopropyl carbonate where the epoxide product might reasonably be expected to be a mixture of about equal amounts of the two possible compounds, surprisingly, the epoxide with the longer carbon chain, propylene oxide in the example cited, is produced as by far the predominant epoxide product, a molar excess of up to 10–15/1 being typical.

DETAILED DESCRIPTION OF THE INVENTION

As described above, the carbonate starting material of this invention has the formula

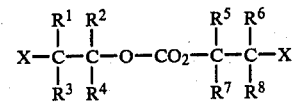

where each of the R groups is hydrogen, a hydrocarbon group, $-CH_2X$, $-CH_2Y$, and each of the adjacent pairs $R^1$, $R^2$ and $R^5$, $R^6$ may form an alkylene group of 3-6 carbon atoms, each X individually is Cl or Br, and Y is an alkoxy group, preferably of 1-4 carbon atoms, or an aroxy group such as a phenol or bisphenol residue. Thus the primary epoxide product can be

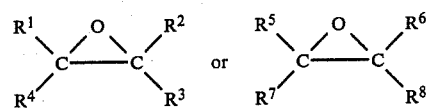

while the principal alkylene dihalide co-product would be either

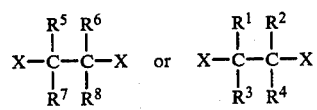

respectively, depending upon the relative sizes of the haloalkyl groups in the starting carbonate.

The term hydrocarbon group as used above to define the R groups includes alkyl groups of one to about 20 carbon atoms, cycloalkyl and alkylcycloalkyl groups of 5–10 carbon atoms, and aromatic hydrocarbon groups of 6–10 carbon atoms.

As can be seen from the above description, this process produces two useful kinds of product, alkylene dihalide and epoxide, assuming $CO_2$ to be a waste product. The structure of the starting carbonate, therefore, is normally designed to produce not only the desired epoxide, but also a particular useful alkylene dihalide which has a boiling point sufficiently different from the epoxide to facilitate easy and complete separation of these two products.

As noted previously, when the two haloalkyl groups in the carbonate molecule are different, two different epoxides and two different alkylene dihalides are produced by the decomposition, the proportions of these products depending upon the relative sizes of the two alkyl groups. Thus, when 2-chloroethyl 1-chloro-2-propyl carbonate is subjected to the conditions of the decomposition process, the principal epoxide and dihalide products are propylene oxide and ethylene dichloride with minor amounts of ethylene oxide and propylene dichloride being formed. Ordinarily, conventional distillation of the mixed products provides effective separation of the individual components as pure compounds.

When a symmetrical bis($\beta$-haloalkyl) carbonate is decomposed by this process, obviously only one epoxide and one alkylene dihalide are formed. For example, the decomposition of bis(2-chloroethyl) carbonate yields ethylene oxide and ethylene dichloride. The advantage of this process in either case over the alkyl $\beta$-haloalkyl carbonate decomposition described in our prior related application is essentially the greater economic value of the alkylene dihalide product of this process as compared to the value of the lower alkyl halide product of the other process.

This process is ordinarily of most interest as a means of producing epoxides of higher molecular weight than ethylene oxide such as propylene oxide, epichlorohydrin, and alkyl or aryl glycidyl ethers. It has particular advantage as mentioned elsewhere in that the halide co-product is not a useless inorganic waste material but rather an economically desirable alkylene dihalide. The minor by-products, usually ethylene oxide and another alkylene dihalide, are readily recoverable and, of course, are also valuable compounds.

The decomposition reaction takes place in the presence of the quaternary salt catalyst at some rate at any temperature from about room temperature to about 250° C., but for normally practical reaction times, the decomposition is preferably carried out at about 150° C.–250° C. Reaction times can range from 0.001 hour to about 10 hours depending on the structure of the carbonate, the temperature, and the nature and amount of the catalyst.

Substantially any quaternary ammonium or phosphonium salt can catalyze the decomposition reaction. Preferably, these salts have the general formula $R_4AZ$ where each R is a hydrocarbon moiety; A is a quaternized nitrogen or phosphorus atom; and Z is an inert (i.e., inert in this process) neutralizing anion which may be inorganic, e.g., chloride, bromide, iodide, bicarbonate, sulfate, or the like; or Z may be an organic ion such as formate, acetate, benzoate, phenate, or bisphenolate. The R groups may be alkyl, aryl, alkaryl, aralkyl, or cycloalkyl. Also, two R groups may combine to form a heterocyclic ring. Illustrative quaternary salt catalysts are tetrabutylammonium bromide, benzyltriethylammonium chloride, N-methylpyridinium chloride, N,N-dibutylmorpholinium iodide, N-propylpyrrolium chloride, tetrabutylphosphonium bromide, tributylmethylphosphonium formate, tetrapropylphosphonium bisulfate, and corresponding ammonium and phosphonium salts with these and other such inorganic and organic neutralizing anions as described above. The catalytic salt may be added as such to the reaction mixture or it may be formed in situ.

Also, amine and phosphine salts such as tributylamine hydrochloride which are a form of quaternary salt will catalyze the reaction although these are generally less desirable in the reaction mixture. Similarly, when a nitrogen-containing solvent such as N,N-dimethylformamide or N,N-dimethylacetamide is employed in the process, the small amount of quaternary salt formed by interaction of the amide nitrogen atom with the halide reactant (or dihalide product) is sufficient to catalyze the decomposition reaction.

Although any significant amount of such a quaternary salt will catalyze the decomposition reaction to some extent, for practical reasons in batch operations, it is preferred to use about 0.1–10 mole percent of the salt based on the carbonate. More quaternary salt catalyst can be used but the excess confers little added advantage and may in fact be disadvantageous.

In a mode of the invention particularly adapted to continuous operation, one or more R groups may be pendant methylene groups from a resin matrix so that the quaternary salt is a salt form of a strong base anion-exchange resin such as DOWEX ® 21K, DOWEX ® 11, DOWEX ® MSA-1, or other such commercially available ion-exchange resins or the phosphonium equivalents of such quaternary ammonium-substituted resins. In such a continuous operation of the process, the $\beta$-haloalkyl carbonate starting material can be passed at an appropriate flow rate through a bed of the strong base anion resin maintained at a suitable temperature within the limits previously defined. Similarly, a solid particulate catalyst can be formed by depositing a quaternary ammonium or phosphonium salt as described above on silica, alumina, clay, a zeolite, or other such inert support.

A reaction solvent or diluent is usually of no advantage and the process is ordinarily run in the absence of such an inert additive. In some cases, however, a solvent may be of some advantage. Inert solvents suitable for use include hydrocarbons such as toluene, xylene, and decane; glycol diethers such as dimethyloxyethane, substituted amides such as N,N-dimethylformamide, and cyclic compounds such as tetrahydrofuran and sulfolane.

In the preparation of higher boiling epoxides particularly, separation of the epoxide product may be facilitated by running the reaction under appropriately reduced pressure or by passing a stream of nitrogen or other inert gas through or over the reaction mixture.

The $\beta$-halogenated alkyl carbonate starting materials for this process can be prepared by several known procedures. The reaction of a chloroformate with an alcohol conventionally used for the preparation of carbonate esters is readily adapted to the preparation of these halogenated carbonates by using the appropriate halogenated alcohol and halogenated alkyl chloroformate reactants. Symmetrical bis(haloalkyl) carbonates in particular can be made by the strong acid catalyzed transesterification reaction of a halogenated alcohol in excess with a dialkyl carbonate. Some of these carbonates can also be made by using an appropriate unsaturated alcohol in the transesterification reaction and then adding halogen or hydrogen halide to the unsaturated ester product. A method recently described in Japanese Pat. No. 46,921/78 whereby a cyclic carbonate such as ethylene carbonate or propylene carbonate is reacted at moderate temperature with an olefin and chlorine or bromine in equal molar amounts is another means of obtaining the halogenated alkyl carbonate starting materials of this invention. By using ethylene carbonate (which is made from ethylene oxide) and an olefin other than ethylene as reactants in the cited Japanese process to make the haloalkyl carbonate starting material of this invention, the present process becomes essentially a means for transferring the epoxide value of ethylene oxide to higher olefins using organic carbonates as intermediates.

Examples 1-10 illustrate the reaction of unsymmetrical haloalkyl alkyl carbonates as claimed in our prior related application noted above.

EXAMPLE 1

A mixture of 4.57 g of 1-chloro-2-propyl methyl carbonate (contained 20-30 percent of the 2-chloro-1-propyl isomeric ester) and 0.034 g of tetrabutylphosphonium bromide in a 10 ml reaction flask was heated by an oil bath at 180° C.-185° C. for 2 hours. The flask was equipped with a magnetic stirrer, a condenser, and a receiver plus a trap, each of the latter containing 10 g of chloroform cooled to −60° C. After 2 hours of heating, the residue in the reaction flask amounted to 0.23 g of material which contained less than 5 percent starting carbonate. The receiver and trap had gained a total of 2.5 g of reaction products which were determined by nuclear magnetic resonance spectroscopic and chromatographic analysis to be a mixture of propylene oxide and methyl chloride, some methyl chloride having been lost because of its high volatility. The conversion of chloropropyl methyl carbonate was nearly 100 percent and the analyses indicated a yield of about 95 percent of the theoretical for propylene oxide.

EXAMPLES 2-3

The procedure of Example 1 was repeated twice using 0.027 g of tetrabutylammonium chloride and 0.037 g of tetrabutylammonium iodide respectively in place of the phosphonium salt catalyst. In each case, the yield of propylene oxide was 97-99 percent of the theoretical amount but the conversion of starting carbonate was relatively low, about 20 percent and 25 percent respectively.

EXAMPLE 4

A mixture of 4.16 g of 2-chloroethyl methyl carbonate and 0.034 g of tetrabutylphosphonium bromide was heated at 180° C. for 3 hours in the apparatus previously described. A carbonate conversion of 99.7 percent was obtained with an 89 percent yield of ethylene oxide.

EXAMPLE 5

In the same way, a mixture of 5.49 g of 2-bromoethyl methyl carbonate and 0.034 g of tetrabutylphosphonium bromide was heated for 6 hours at 200° C. to produce a carbonate conversion of 100 percent and an 88 percent selectivity to ethylene oxide and methyl bromide.

EXAMPLE 6

A mixture of 3.34 g of 1-chloro-2-octyl methyl carbonate (containing 21 percent of the corresponding 2-chloro-1-octyl ester) and 0.024 g of tetrabutylphosphonium formate was heated as above at 200° C.-205° C. for 2 hours at reduced pressure (200 mm Hg). An isolated yield of 96 percent of theory of 1,2-epoxyoctane was collected in the receiver.

EXAMPLE 7

A mixture of 2.89 g of 2-chlorocyclohexyl methyl carbonate and 0.039 g of tetrabutylphosphonium salt of Bisphenol A was heated at 200° C.-205° C. for 1.5 hours. A yield of 1.34 g of 1,2-epoxycyclohexane was collected in the receiver.

EXAMPLE 8

In a procedure similar to that used in Example 6, a mixture of 3.89 g of 2-bromo-1-phenylethyl methyl carbonate and 0.024 g of tetrabutylphosphonium formate was heated at 180° C. for 2 hours at 50 mm Hg absolute pressure. The product condensed in the receiver was 1.58 g of a mixture containing 40 percent styrene oxide and 60 percent phenylacetaldehyde.

EXAMPLE 9

The reduced pressure technique of Examples 6 and 8 was followed in heating a mixture of 5.61 g of 1,3-dichloro-2-propyl methyl carbonate and 0.078 g of the tetrabutylphosphonium Bisphenol A salt used in Example 7. After 2 hours at 195° C.-200° C. and 100 mm Hg absolute pressure, 2.85 g of 88 percent pure epichlorohydrin had condensed in the receiver.

EXAMPLE 10

To a 4-neck 50 ml reaction flask equipped with a mechanical stirrer, addition funnel, distillation head, and nitrogen inlet there was added 0.24 g of tetrabutylphosphonium formate and the flask was heated to 185° C.-190° C. with a stream of 30 ml/min. of nitrogen passing through while 2.81 g of 2,3-dichloro-1-propyl methyl carbonate was added over a period of 30 minutes. Analyses of 1.4 g of condensed effluent in the receiver cooled by solid $CO_2$ and 0.47 g of residue indicated a 90-95 percent conversion of carbonate with a 50-60 percent yield of epichlorohydrin.

Examples 11-15 demonstrate the decomposition of halogenated alkyl carbonates under the conditions described above to make vicinal epoxides and alkylene dihalides.

EXAMPLE 11

A mixture of 3.02 g (0.015 g mole) of 2-chloroethyl 1-chloro-2-propyl carbonate and 0.051 g (0.00015 g mole) of tetrabutylphosphonium bromide was heated at 190° C.-192° C. in a 10 ml reaction flask equipped with magnetic stirrer and a distillation head connected to a receiver containing 11.9 g of chloroform cooled to −60° C. The 2-chloroethyl 1-chloro-2-propyl carbonate starting material was prepared by reacting 1.5 moles of ethylene carbonate with about two moles each of propylene and chlorine at about room temperature as shown in Japanese Pat. No. 46,921/78. After 3 hours of heating, a residue of 0.20 g remained in the reaction flask and the receiver had gained 2.15 g in total weight. Nuclear magnetic resonance spectroscopic and chromatographic analyses of the reaction products indicated that 97 percent of the starting carbonate had been converted to a mixture of 83 percent of the theoretical quantity of propylene oxide and 6 percent of the theoretical amount of ethylene oxide together with corresponding yields of 1,2-dichloroethane and 1,2-dichloropropane, respectively.

EXAMPLE 12

The procedure of Example 11 was repeated except for using five times the amount (0.255 g) of tetrabutylphosphonium bromide catalyst and heating the reaction mixture only one hour at the indicated temperature. A 97 percent conversion of the starting carbonate was obtained with 74 percent yield of propylene oxide and 6 percent yield of ethylene oxide together with 86 percent yield of ethylene dichloride and 9 percent yield of propylene dichloride.

EXAMPLE 13

The procedure of Example 11 was repeated except that 0.25 g of DOWEX ® MSA-1 ion-exchange resin was used as the catalyst. This resin is a strong base anion resin consisting of a macroporous cross-linked styrene polymer matrix having pendant quaternary ammonium chloride functionalities.

After 2 hours of heating, 33 percent of the starting carbonate had been converted to a mixture of propylene oxide in 56 percent yield and ethylene oxide in 5 percent yield plus a 76 percent yield of ethylene dichloride and a 12 percent yield of propylene dichloride.

EXAMPLE 14

To a 25 ml reaction flask equipped with an addition funnel and a distillation head with receiver there was added 0.54 g of the mono(tetrabutylphosphonium) salt of Bisphenol A complexed with a molecule of the free bisphenol. The flask was heated to 190°–192° C. as 3.53 g (0.015 g mole) of a 2-chloroethyl 1,3-dichloro-2-propyl carbonate was added portionwise over 2 hours with the flask and receiver maintained at 150 mm Hg absolute pressure. The carbonate starting material was made by reacting 1,3-dichloro-2-propanol with 2-chloroethyl chloroformate under conventional alcohol chloroformate reaction conditions. The receiver was cooled with solid $CO_2$. Analyses of the 2.61 g condensed effluent in he receiver and the 0.71 g of residue in the reaction flask indicated about 95 percent conversion of the starting carbonate with about 50–55 percent yield of epichlorohydrin.

EXAMPLE 15

Following the procedure of Example 14, 3-tert-butoxy-1-chloro-2-propyl 2-chloroethyl carbonate (from the reaction of 3-tert-butoxy-1-chloro-2-propanol with 2-chloroethyl chloroformate) is heated in the presence of tetrabutylphosphonium bromide to produce tert-butyl glycidyl ether and ethylene dichloride as the principal reaction products.

EXAMPLE 16

By reacting 3-phenoxy-1-chloro-2-propanol with 2-chloroethyl chloroformate according to conventional chloroformate ester reaction procedures, 2-chloroethyl 3-phenoxy-1-chloro-2-propyl carbonate is obtained.

When the latter compound is heated in the presence of a phosphonium or ammonium salt catalyst as shown in the foregoing examples, phenyl glycidyl ether is produced as the principal epoxide product.

When the chlorinated carbonate ester starting materials shown in Examples 11–16 are replaced by the corresponding bromo or mixed bromo chloro esters, similar results are obtained by following the indicated procedures. For example, 2-bromoethyl 1-bromo-2-propyl carbonate is thereby decomposed to form propylene oxide and ethylene dibromide as the principal epoxide and dihalide products, while 2-bromoethyl 1-chloro-2-propyl carbonate decomposes in the same way to produce propylene oxide and 1-bromo-2-chloroethane as the principal reaction products.

We claim:

1. A process for making a vicinal epoxide and an alkylene dihalide which comprises contacting a carbonate ester of the formula

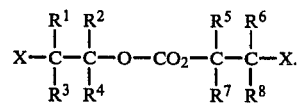

wherein the R groups are individually hydrogen, a hydrocarbon group, $-CH_2X$, $-CH_2Y$ and each of the pairs $R^1$, $R^2$ and $R^5$, $R^6$ may together form an alkylene group of 3–6 carbon atoms, each X is Cl or Br, and Y is an alkoxy or aroxy group, with a quaternary ammonium or phosphonium salt catalyst at about 25° C.–250° C. and separating said epoxide from the reaction mixture.

2. The process of claim 1 wherein the temperature is about 150° C.–250° C.

3. The process of claim 2 wherein $R^3$, $R^4$, $R^5$, $R^6$, $R^7$ and $R^8$ are hydrogen and X is Cl.

4. The process of claim 3 wherein one of $R^1$ and $R^2$ is a methyl group and the other is hydrogen and the principal epoxide product is propylene oxide.

5. The process of claim 3 wherein one of $R^1$ and $R^2$ is a chloromethyl group and the other is hydrogen and the principal epoxide product is epichlorohydrin.

6. The process of claim 3 wherein $R^1$ is a lower alkoxymethyl group, $R^2$ is hydrogen, and the principal epoxide product is a lower alkyl glycidyl ether.

7. The process of claim 6 wherein $R^1$ is a tert-butoxymethyl group and the principal epoxide product is tert-butyl glycidyl ether.

8. The process of claim 3 wherein $R^1$ is an aroxymethyl group, $R^2$ is hydrogen, and the principal epoxide product is the aryl glycidyl ether.

9. The process of claim 8 wherein $R^1$ is a phenoxymethyl group and the principal epoxide product is phenyl glycidyl ether.

10. The process of claim 2 wherein the salt catalyst is a strong base anion-exchange resin having quaternary ammonium halide functionalities.

* * * * *